United States Patent
Cho et al.

(10) Patent No.: US 6,490,029 B1
(45) Date of Patent: Dec. 3, 2002

(54) AUTOMATIC ANALYSIS METHOD OF CRUDE PETROLEUM OILS USING SPECTROSCOPY

(75) Inventors: In-Ho Cho, Ulsan (KR); Jin-Kyu Choi, Ulsan (KR); Hoe-Il Chung, Ulsan (KR)

(73) Assignee: S.K. Corporation, Seoul (KR)

( * ) Notice: Subject to any disclaimer, the term of this patent is extended or adjusted under 35 U.S.C. 154(b) by 0 days.

(21) Appl. No.: 09/869,438

(22) PCT Filed: Dec. 22, 1999

(86) PCT No.: PCT/KR99/00907

§ 371 (c)(1), (2), (4) Date: Jun. 25, 2001

(87) PCT Pub. No.: WO00/39561

PCT Pub. Date: Jul. 6, 2000

(30) Foreign Application Priority Data

Dec. 28, 1998 (KR) .............................. 98-59508

(51) Int. Cl.⁷ .................. G01N 33/28; G01J 3/44; G01J 3/28; G01J 5/02
(52) U.S. Cl. ................ 356/70; 356/301; 356/326; 250/339.12
(58) Field of Search .................. 356/70, 36, 301, 356/326, 327, 328, 339.12

(56) References Cited

U.S. PATENT DOCUMENTS

| | | | |
|---|---|---|---|
| 4,405,442 A | * 9/1983 | Deschamps et al. | 208/107 |
| 4,664,785 A | * 5/1987 | Devos et al. | 208/353 |
| 5,206,701 A | * 4/1993 | Taylor et al. | 356/325 |
| 5,223,715 A | * 6/1993 | Taylor | 250/343 |
| 5,419,185 A | * 5/1995 | Chimenti et al. | 73/54.01 |
| 5,475,612 A | * 12/1995 | Espinosa et al. | 700/268 |
| 5,504,331 A | * 4/1996 | Lane et al. | 250/339.09 |
| 6,012,019 A | * 1/2000 | Saby | 702/32 |
| 6,140,647 A | * 10/2000 | Welch et al. | 250/339.12 |

FOREIGN PATENT DOCUMENTS

| | | | | |
|---|---|---|---|---|
| JP | 07082573 A | * 3/1995 | | C10G/7/00 |
| JP | 08266802 A | * 10/1996 | | B01D/3/42 |

* cited by examiner

Primary Examiner—Stephone B. Allen
Assistant Examiner—Eric J Spears
(74) Attorney, Agent, or Firm—Abelman, Frayne & Schwab

(57) ABSTRACT

Disclosed is an automatic analysis method of crude oils, using spectroscopy. A near infrared spectroscopic analysis apparatus is combined with an ordinary distillation apparatus, so as to analyze the physical properties of each oil distillate as soon as it is separated from crude oils, thereby bringing about a significant improvement in analysis accuracy and in an economical aspect. It takes only two days for one person to obtain a full assay data for crude oils by taking advantage of the method. In addition to requiring a significantly reduced equipment cost, the method enables full assay data for crude oils to be obtained quickly, thereby securing more up-to-date information about crude oils and producing an economical benefit.

3 Claims, 3 Drawing Sheets

AUTOMATIC ANALYSIS METHOD OF CRUDE PETROLEUM OILS USING SPECTROSCOPY

TECHNICAL FIELD

The present invention relates, in general, to a method for automatically analyzing crude petroleum oils using a spectroscopic technique and, more particularly, to an on-line analysis method of crude petroleum oils, which brings about a significant improvement in analysis accuracy and in an economical aspect. In the present invention, a near infrared (NIR) spectroscopic analysis apparatus is combined with an ordinary distillation apparatus, so as to analyze the physical properties of each oil distillate as soon as it is separated from crude oils.

PRIOR ART

For oil refineries, where crude oils are refined to produce high value-added products, it is very important to know information about the crude oils to be treated. There are almost no oil refineries that treat only one kind of a crude oil. Indeed, they refine up to tens of kinds of crude oils per year. To this end, most of the oil refineries have been equipped with analysis apparatuses for crude oils and have engaged a great deal of manpower in obtaining up-to-date analysis data for crude oils. Recently, detail assay data(Full Assay Data) which has information about heavy distillates is required as heavy oil cracking facilities are widely introduced. In order to produce full assay data, highly expensive distillation and analysis apparatuses are needed, along with much manpower. Usually, the full assay data, for example, is made by distilling crude oil to more than 10 fractions and analyzing each of the oil fractions for more than 10 physical properties. It typically takes a time of 1–2 weeks to produce full assay data, and about 30% of the period is needed to separate oil fractions through distillation while the remaining 70% is set aside for the analysis of physical properties of each fraction.

DISCLOSURE OF THE INVENTION

As a result of the intensive and thorough research on the crude oil analysis, repeated by the present inventors aiming to reduce the manpower and time period required for the crude oil analysis, it was found that spectroscopy can be introduced to analyze the physical properties of crude oils. In this regard, a physical property-predicting model was established from the spectrometric data from an oil distillate on the basis of the chemometrics theory. By comparing spectrometric data obtained from a target distillate with those of the model, the target distillate could be assayed for physical properties rapidly and accurately. This spectroscopic technique exceptionally reduces the time period required for the analysis of crude oils, compared with conventional assay techniques. Indeed, the measurement of the physical properties of crude distillates can be completed as soon as the crude distillates are separated. In addition, because only a small amount of the distillates are demanded for the spectroscopic measurement, the time period that it takes to distill crude oils is greatly reduced. Accordingly, a significant reduction can be brought about in the amount of analysis equipment as well as the manpower. However, some trace components and physical properties of heavy residue remain unable to be assayed by the spectroscopic method of the invention. Thus, they can be analyzed in conventional manners.

It is therefore an object of the present invention to provide an automatic method for analyzing crude petroleum oils, which utilizes a spectrometric technique in combination with a distillation apparatus in measuring physical properties of crude petroleum oils with the aim of reducing as much equipment cost, manpower and time necessary for the analysis of crude petroleum oils as possible.

Based on the present invention, the above object could be accomplished by a provision of an automatic analysis method of crude oils, using spectroscopy, comprising the steps of: providing analysis equipment comprising: a distillation apparatus comprising: a vacuum part; a heating part; a separation column part; a liquified gas-collecting cylinder having absorbance spectrum-measuring cells; and a distillate-collecting part having a plurality of distillate-collating cylinders; a spectroscopic analyzer comprising: a spectroscope 10 for separating and providing light beams by wavelengths; a measuring cell 9 for measuring samples for absorbance at predetermined wavelengths; and a fiber optic for connecting the spectroscope to the measuring cell; and a physical property predicting model; measuring gaseous components for absorbance at predetermined wavelengths in an on-line manner in the liquified gas-collecting cylinder, said gaseous components being distilled at the first time from a crude oil sample; measuring various distillates of the distillate-collecting cylinders, in sequence, for absorbance at predetermined wavelengths; predicting physical properties of the crude sample from the spectrum data on the basis of the chemometrics theory; and producing assay data for crude oils from the predicted physical properties.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

The application of the preferred embodiments of the present invention is best understood with reference to the accompanying drawings.

Figure 1:
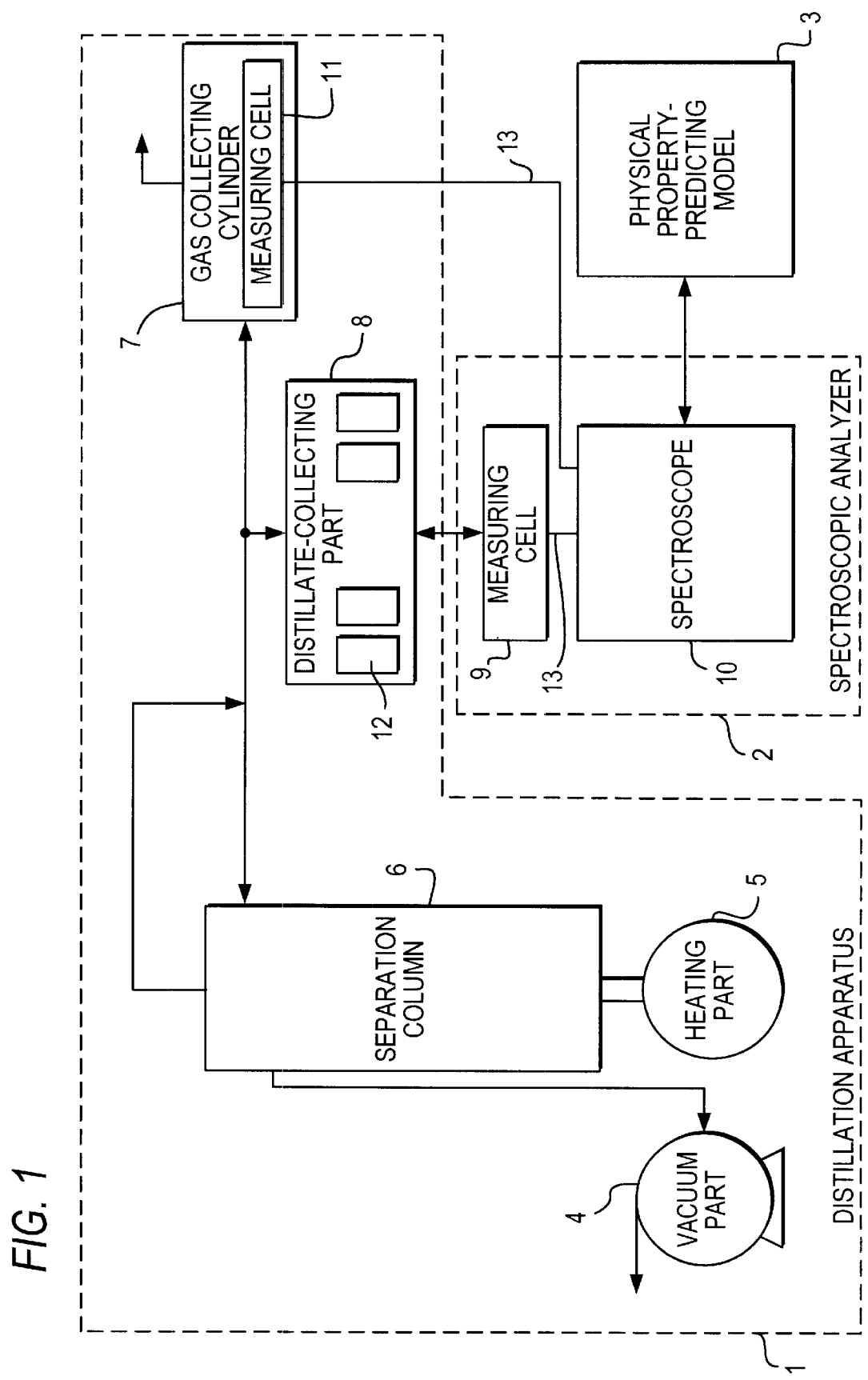
FIG. 1 is a schematic diagram illustrating an automatic, analysis apparatus of crude oils, useful in the method of the present invention.

The analysis equipment used in the present invention is comprised of three divisions: distillation apparatus 1; spectroscopic analyzer 2; and physical property-predicting model 3, and the overall arrangement of them is shown in FIG. 1.

As shown in FIG. 1, the distillation apparatus 1 comprises a vacuum part 4, a heating part 5, a separation column 6, a liquified gas-collecting cylinder 7, and a distillate-collecting part 8 and is found in almost all oil refineries. To operate the distillation apparatus 1, first, a crude oil sample is fed to the heating part 5. While the crude oil sample is gradually heated in the heating part 5, lighter components of the crude oil are evaporated earlier and rise to the separation column 6 where refluxing is conducted at a certain ratio (usually 1:5). The distillates from the separation column 6 are transferred to the distillate-collecting part 8. While gas distillates, which come out mostly at early stages, are cooled in the liquified gas-collecting cylinder 7, the distillates heavier than C5 are collected in the distillate-collecting part 8. There is a greater possibility to cause the thermal cracking of crude oils as the temperature of the heating part 5 increases. To avoid the thermal cracking, the vacuum part 4 operates to lower the operation pressure of the separation column 6. The low pressures allow the crude oils to be distilled and separated at low temperatures. In the initial stage, the heating is conducted at atmospheric pressure. The pressure of the separation column 6 is reduced to 2 torr in the separation stages of 400° C. (on the basis of the atmospheric pressure). When the temperature is further elevated, the pressure reduction continues to be conducted to an extent of 0.1 torr. In the distillate-collecting part 8, the distillates are separated according to predetermined temperatures and their production yields are calculated.

Figure 2:
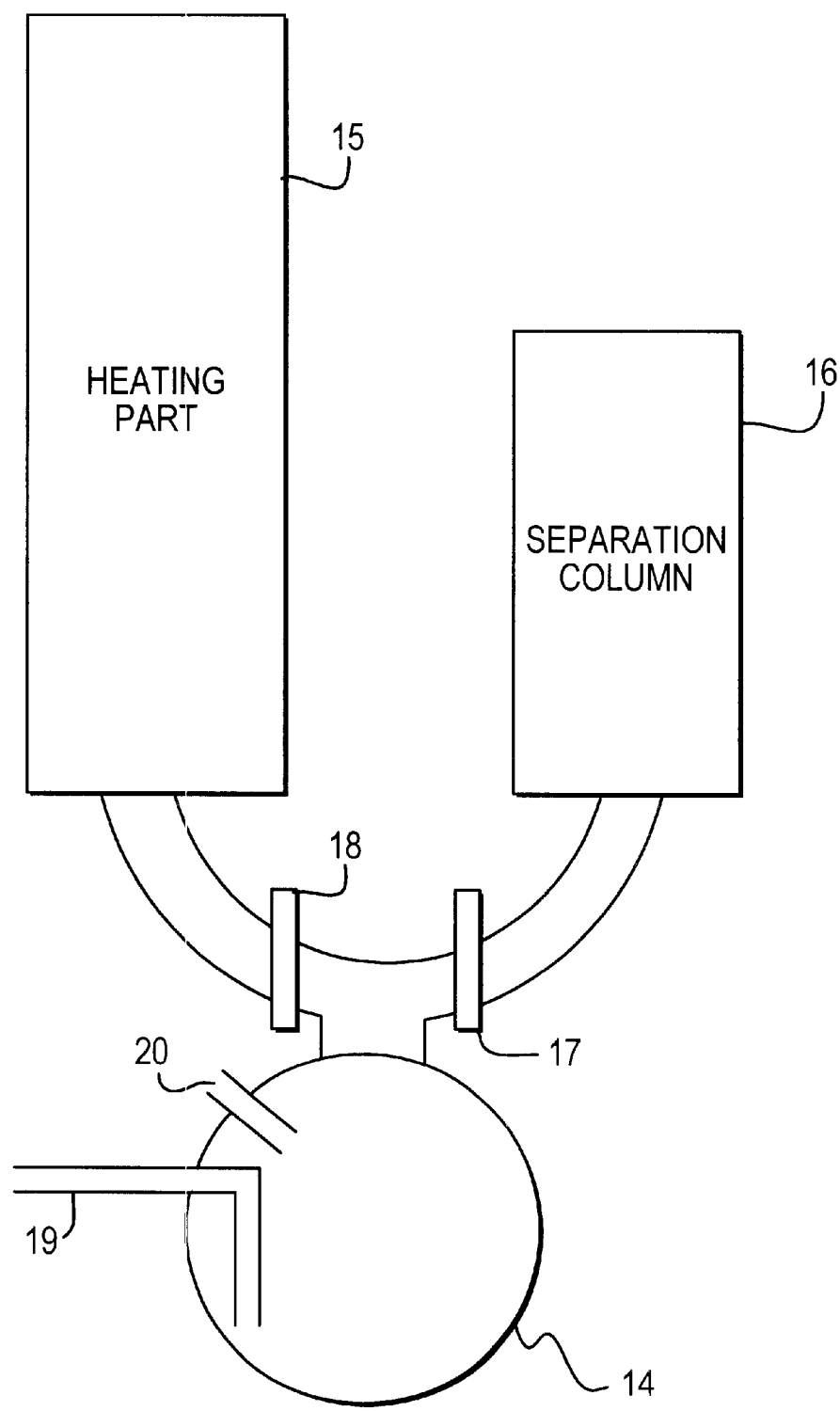
FIG. 2 is a schematic diagram illustrating separation columns, according to an embodiment of the present invention.

Typically, the distillation apparatus 1 has an ability to separate a broad spectrum of distillates ranging from gas distillates to 565° C. distillates. The distillates which come out at 400° C. or lower are treated in the same separation column. For the distillates which come out at higher than 400° C., the distillation is usually carried out at ultravacuum conditions (about 0.1 torr). In this regard, a separation column is additionally employed. In the present invention, automation can be achieved even when two separation columns are used. This automation is embodied in FIG. 2. As shown in FIG. 2, shutoff valves 17 and 18 are used to alternatively operate a separation column 15 for 400° C. or less distillates and a separation column 16 for 400° C. or higher distillates, holding the heating part 15 in common. In detail, when separating 400° C. or less distillates, the shutoff valve 17 is closed while the distillates are separated in the column 15. On the other hand, the shutoff valve 18 is closed to allow 400° C. or higher distillates to be separated through the column 16. Before the separation of 400° C. or higher distillates is initiated, the heating part 15 is pressurized with nitrogen via a pressure pipe 20 to take a part of the residual sample through a sampling pipe 19. This sample is used for the analysis of 400° C.+ physical properties.

Figure 3:
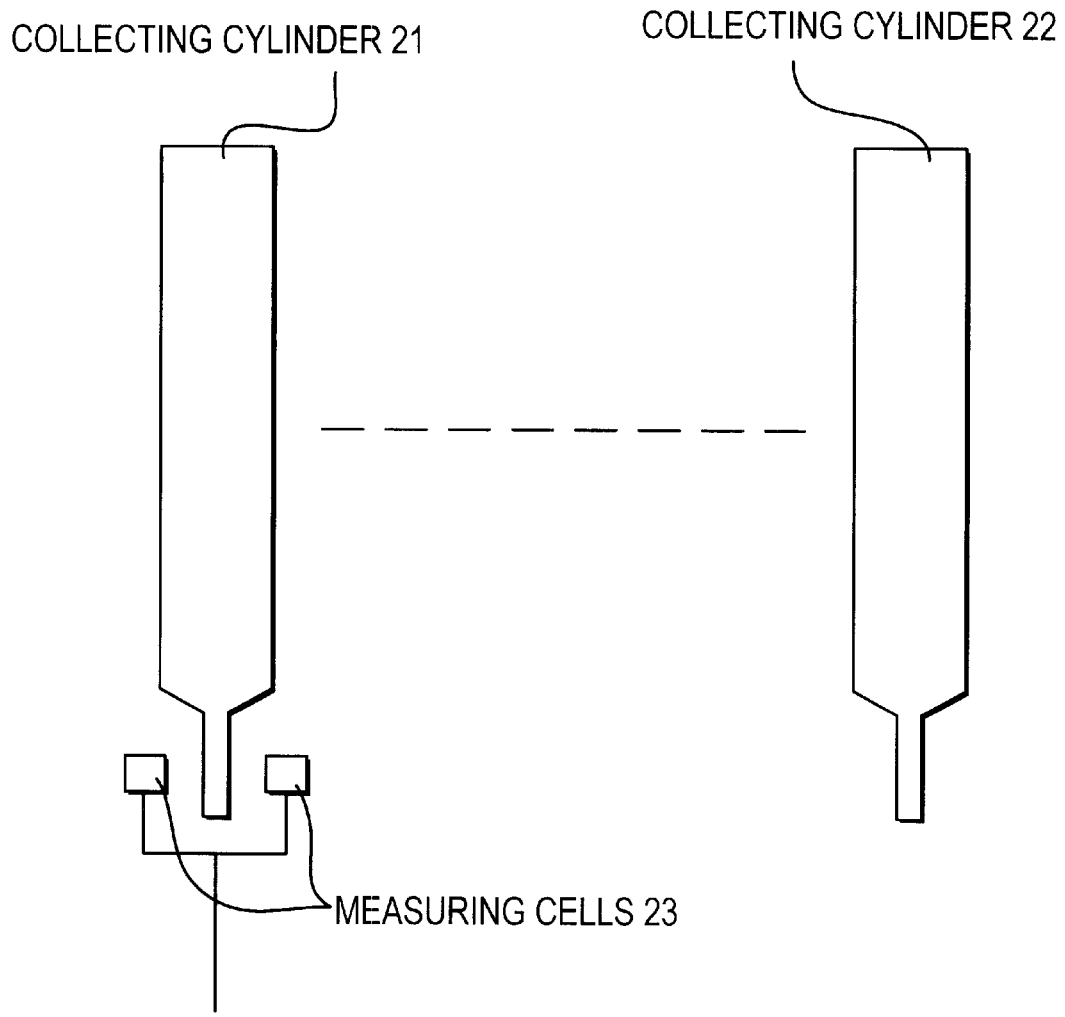
FIG. 3 is a schematic diagram illustrating a distillate-collecting part according to an embodiment of the present invention.

As for the spectroscopic analyzer 2, it may use near IR beams as measuring means. This near IR spectroscopic analyzer is composed of a spectroscope 10 for separating and providing near IR beams by wavelengths and a measuring cell 9 for measuring the absorption spectra of samples, as shown in FIG. 1. The measuring cell 9 is connected through a fiber optic 13 to the spectroscope 10. Usually, the distillate-collecting part 8 of the distillation apparatus 1 is able to separate and collect at least 10 distillates. Accordingly, the measuring cell 9 is structured to automatically measure the absorbances of the collected distillates, respectively. The automation technique related to this point can be easily found in various analyzers used in, for example, gas chromatography. FIG. 3 shows an embodiment of automatically measuring the absorbance of each distillate. As shown, a plurality of regularly spaced, collecting cylinders 21 and 22, each having a measuring part, are, in sequence, measured for absorbance at predetermined wavelengths by the measuring cells 23 while being rotated.

The gas components from methane to normal pentane, which come out at the very first upon distillation of crude oils, are cooled and liquified by use of dry ice in the distillation apparatus and then, collected in a collecting cylinder. For conventional crude oil analyzers, the collecting cylinder is subjected to, for example, gas chromatography by human. In the present invention, the liquified gas-collecting cylinder 7 is additionally provided with a measuring cell 11 so that near IR absorption spectra of the liquified gas can be automatically obtained with no manual aid. Thus, the present invention minimizes manual operation of gas distillates, so as to improve the accuracy of measured data and reduce the manpower and time period necessary for the analysis.

Alternatively, the spectroscopic analyzer may be selected from an IR spectrometer, a Raman spectrometer and an NMR spectrometer, instead of the near IR spectrometer.

While the spectroscopic analyzer is nothing but to measure the absorbance of samples at predetermined wavelengths, the physical property-predicting model 3 functions to embody the spectrum data into physical properties. For 75–155° C. distillates and 235–350° C. distillates, the physical properties were predicted from the model and are given in Table 1, below, along with those obtained by a conventional analysis technique. For example, the octane value of the 75–155 distillates was measured to be 41.0 when using a conventional technique (octane engine test) and 41.1 when using the present invention. As apparent from Table 1, the accuracy of all of the predicted values is within the permission range according to ASTM.

In order to establish the physical property-predicting model, many samples are measured for physical properties in a conventional method as well as for near IR spectra, followed by determining the relationship between the physical properties and the spectra on the basis of the chemometrics theory. Once the model is established, physical properties of subsequent samples can be predicted simply from their spectrum data in view of the model. For practical use, predicting models should be established according to sample kinds and physical properties. The physical property-predicting model 3 of FIG. 1 is a set of models which allow the prediction of the physical properties of each distillate. Details directed to the chemometrics theory on which the physical property-predicting model is based can be referred to the following literature: H. Martens and T. M. Naes, Multivariate Calibration, p 116, John Wiley and Sons, New York, 1989; and K. R. Beebe, R. J. Pell, and M. B. Searholtz, Chemometrics, John Wiley and Sons, New York, 1998.

TABLE 1

| Physical Properties | Distillates (° C.) | | | |
| --- | --- | --- | --- | --- |
| | 75~155 (Exp) | 75~155 (NIR) | 235~350 (Exp) | 235~350 (NIR) |
| API | 61.3 | 61.3 | 26.1 | 26.2 |
| Total Paraffin (%) | 72.7 | 73.0 | — | — |
| n-paraffin (%) | 33.8 | 33.6 | — | — |
| I-paraffin (%) | 38.9 | 39.4 | — | — |
| Naphthene (%) | 17.5 | 17.3 | — | — |
| Aromatic (%) | 9.8 | 9.7 | — | — |
| Smoke point (mm) | — | — | — | — |
| R. Vapor Point (psi) | 2.5 | 2.5 | — | — |
| Aniline Point (° C.) | 53.8 | 53.6 | 71.2 | 71.4 |
| Reflec. Index (@ 20° C.) | 1.4118 | 1.4121 | 1.4704 | 1.4700 |
| Octane No. | 41.0 | 41.1 | — | — |
| Cetane No. | — | — | 52 | 51.3 |
| Flow Point (° C.) | — | — | −12.5 | −13.0 |
| Cloud Point (° C.) | — | — | −8.0 | −7.7 |
| Freezing Point (° C.) | — | — | — | — |
| CFPP (° C.) | — | — | −10.0 | −10.5 |
| Viscosity @ 40° C. (cSt) | — | — | 3.72 | 3.67 |
| Viscosity @ 50° C. (cSt) | — | — | — | — |
| Viscosity @ 100° C. (cSt) | — | — | — | — |
| Flash Point (pmcc, ° C.) | — | — | 120 | 119 |
| Residual C (%) | — | — | — | — |

TABLE 1-continued

| Physical Properties | Distillates (° C.) | | | |
|---|---|---|---|---|
| | 75~155 (Exp) | 75~155 (NIR) | 235~350 (Exp) | 235~350 (NIR) |
| Asphaltenes (%) | — | — | — | — |
| BMCI | — | — | — | — |
| D86 5% Distil. Point (° C.) | 104.3 | 102.1 | 264.2 | 261.3 |
| D86 10% Distil. Point (° C.) | 106.2 | 104.9 | 266.7 | 263.9 |
| D86 30% Distil. Point (° C.) | 114.4 | 113.3 | 275.7 | 274.3 |
| D86 50% Distil. Point (° C.) | 117.2 | 117.1 | 286.2 | 285.5 |
| D86 70% Distil. Point (° C.) | 125.5 | 124.6 | 301.4 | 300.1 |
| D86 90% Distil. Point (° C.) | 137.5 | 135.8 | 319.9 | 321.2 |
| D86 95% Distil. Point (° C.) | 140.7 | 138.3 | 325.8 | 327.9 |

A better understanding of the present invention may be obtained in light of the following example which is set forth to illustrate, but is not to be construed to limit the present invention.

EXAMPLE I

Assay data for crude oil was obtained in a manual measuring method and are given in Table 2, below. In addition, the same crude oil was measured according to the present invention to give assay data which are shown in Table 3, below.

As apparent from the Tables 2 and 3, these two results agree with each other within the ASTM range. In the aspect of the analysis time period, the present invention was found to have an advantage over the conventional technique. Although it depends on the quantity of manpower and equipment, the analysis time period was 10 days when the manual technique was used. On the other hand, it took only 2 days for the present invention to produce the assay data. In Table 3, the items marked by ○ were not accurately analyzed by the near IR spectroscopic method of the present invention. However, these items are believed to be measured in an automatic manner as a better advance is achieved in such a spectroscopic technique.

It should be understood that the number and temperature ranges of the separated distillates used in this example may be altered according to the necessity of users. Of course, this is also true for the physical properties to be measured.

TABLE 2

| Physical Properties | Distillates (° C.) | | | | | | | |
|---|---|---|---|---|---|---|---|---|
| | C5~75 | 75~155 | 155~190 | 190~235 | 235~350 | 350~360 | 360~538 | 538+ |
| API | 73.6 | 47.6 | 41.5 | 37.9 | 31.5 | 29.6 | 25.2 | 20.5 |
| Total S (%) | <0.01 | <0.01 | <0.01 | 0.02 | 0.06 | 0.13 | 1.12 | 0.15 |
| Paraffin (vol %) | 72.95 | 41.06 | 34.67 | — | — | — | — | — |
| n-paraffin | 32.67 | 27.35 | 19.13 | — | — | — | — | — |
| I-paraffin | 40.28 | 13.71 | 15.54 | — | — | — | — | — |
| Naphthene | 19.05 | 38.52 | 12.19 | — | — | — | — | — |
| Aromatic | 8.01 | 20.42 | 53.15 | — | — | — | — | — |
| Smoke point | — | — | 16 | 14 | — | — | — | — |
| R. Vapor Pressure | 12.76 | 2.13 | — | — | — | — | — | — |
| Aniline Point | — | 19.7 | 27.1 | 48.8 | 63.7 | 80.6 | — | — |
| Reflect. Index | — | 1.4390 | 1.4574 | 1.4640 | 1.4837 | — | 1.4926 | — |
| Octane No. (RON) | 80.4 | 78.8 | — | — | — | — | — | — |
| Cetane No. | — | −4.9 | 19.8 | 34.8 | 43.9 | 47.7 | — | — |
| Pour Point (° C.) | — | — | — | — | −10.0 | 22.5 | 45.0 | 45 |
| Cloud Point | — | — | — | — | −7.0 | 27 | — | — |
| Freezing Point | — | — | <−70 | −47 | — | — | — | — |
| CFPP | — | — | — | — | −9.0 | 24 | — | — |
| Flash Point (° C.) | — | — | 36 | 74 | 117 | 186 | — | — |
| N (PPM) | — | — | — | — | — | — | 412 | 848 |
| Residual C (wt %) | — | — | — | — | — | — | — | 3.86 |
| Asphaltenes (wt %) | — | — | — | — | — | — | — | 0.95 |
| Ni (wt PPM) | — | — | — | — | — | — | — | 3.0 |
| V (wt PPM) | — | — | — | — | — | — | — | <1.0 |
| Fe (wt %) | | | | | | | | 9.0 |
| Viscos. (37.8° C.:cSt) | | | | 1.47 | 3.59 | 9.84 | | |
| Viscos. (50° C.:cSt) | — | — | — | — | — | 6.86 | 26.35 | 109 |
| Distil. Point 5% (° C.) | 43.5 | 102 | 160.3 | 202.3 | 261.4 | — | 390.2 | — |
| Distil. Point 10% | 46.5 | 104 | 161.0 | 202.8 | 264.2 | — | 401.9 | — |
| Distil. Point 30% | 52.0 | 109 | 163.1 | 206.1 | 269.9 | — | 417.7 | — |
| Distil. Point 50% | 57.5 | 115 | 165.3 | 209.4 | 277.8 | — | 435.2 | — |
| Distil. Point 70% | 63.5 | 123.5 | 168.3 | 213.7 | 290.3 | — | 450.3 | — |
| Distil. Point 90% | 69.5 | 136.5 | 173.7 | 220.5 | 311.2 | — | 482.5 | — |
| Distil. Point 95% | 72.5 | 141.0 | 177.2 | 223.3 | 319.0 | — | 496.7 | — |

TABLE 3

| Physical Properties | Distillates (° C.) | | | | | | | |
|---|---|---|---|---|---|---|---|---|
| | C5~75 | 75~155 | 75~190 | 190~235 | 235~350 | 350~360 | 360~538 | 538+ |
| API | 73.8 | 47.9 | 41.5 | 37.84 | 31.6 | 29.63 | 25.4 | ○ |
| Total S (%) | ○ | ○ | ○ | ○ | ○ | ○ | ○ | ○ |
| Paraffin (vol %) | 72.34 | 40.54 | 35.0 | — | — | — | — | — |
| n-paraffin | 32.31 | 26.92 | 19.17 | — | — | — | — | — |
| I-paraffin | 40.03 | 13.62 | 15.83 | — | — | — | — | — |
| Naphthene | 19.21 | 38.70 | 12.01 | — | — | — | — | — |
| Aromatic | 8.33 | 19.94 | 53.20 | — | — | — | — | — |
| Smoke point | — | — | 15.3 | 13.5 | — | — | — | — |
| R. Vapor Pressure | 12.86 | 2.14 | — | — | — | — | — | — |
| Aniline Point | — | 19.6 | 27.2 | 49.0 | 63.5 | 80.5 | — | — |
| Reflect. Index | — | 1.4389 | 1.4573 | 1.4640 | 1.4836 | — | 1.4927 | — |
| Octane No. (RON) | 80.6 | 78.6 | — | — | — | — | — | — |
| Cetane No. | — | -4.7 | 20.1 | 35.2 | 43.5 | 47.3 | — | — |
| Pour Point (° C.) | — | — | — | — | -11.3 | 21.3 | 4.71 | — |
| Cloud Point | — | — | — | — | -8.0 | 26.8 | — | — |
| Freezing Point | — | — | <-70 | -46 | — | — | — | — |
| CFPP | — | — | — | — | -9.1 | 25 | — | — |
| Flash Point (° C.) | — | — | 36.4 | 72.8 | 116.6 | 186 | — | — |
| N (PPM) | — | — | — | — | — | — | ○ | ○ |
| Residual C (wt %) | — | — | — | — | — | — | — | ○ |
| Asphaltenes (wt %) | — | — | — | — | — | — | — | ○ |
| Ni (wt PPM) | — | — | — | — | — | — | — | ○ |
| V (wt PPM) | — | — | — | — | — | — | — | ○ |
| Fe (wt %) | | | | | | | | ○ |
| Viscos. (37.8° C.:cSt) | | | | 1.44 | 3.60 | 9.58 | | |
| Viscos. (50° C.:cSt) | — | — | — | — | — | 6.70 | 26.31 | ○ |
| Distil. Point 5% (° C.) | 45.5 | 104 | 160.0 | 201.5 | 263 | — | 393.5 | — |
| Distil. Point 10% | 47.0 | 104.8 | 161.5 | 203.5 | 264.1 | — | 407.2 | — |
| Distil. Point 30% | 55.0 | 109.3 | 162.4 | 207.1 | 269.8 | — | 423.9 | — |
| Distil. Point 50% | 59.0 | 113.2 | 166.3 | 210.2 | 278.7 | — | 443.2 | — |
| Distil. Point 70% | 62.4 | 121.3 | 167.3 | 213.3 | 290.1 | — | 459.0 | — |
| Distil. Point 90% | 70.5 | 138.2 | 173.3 | 221.5 | 313.5 | — | 484.5 | — |
| Distil. Point 95% | 73.4 | 140.3 | 175.9 | 222.5 | 319.8 | — | 490.7 | — |

○ analyzed by conventional experimental equipments

INDUSTRIAL APPLICABILITY

As described hereinbefore, the distillate separation through distillation and the analysis of physical properties of each distillate are separately conducted in conventional analysis methods of crude oils. Thus, they suffer from disadvantages in that high equipment cost and excessive manpower and time are demanded for the analysis. To produce a full assay data including a plurality of 400° C. or higher distillates, for instance, it takes 1–2 weeks for two or more persons by conventional techniques.

When using the method of the present invention, it takes only two days for one person to obtain such a full assay data. In addition to requiring a significantly reduced equipment cost, the present invention enables full assay data for crude oils to be obtained quickly, thereby securing more up-to-date information about crude oils and producing an economical benefit.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An automatic analysis method of crude oils, using spectroscopy, comprising the steps of:
   providing analysis equipment comprising:
      a distillation apparatus comprising:
         a vacuum part;
         a heating part;
         a separation column part;
         a liquified gas-collecting cylinder having absorbance spectrum-measuring cells; and
         a distillate-collecting part having a plurality of distillate-collecting cylinders;
      a spectroscopic analyzer comprising:
         a spectroscope for separating and providing light beams by wavelengths;
         a measuring cell for measuring samples for absorbance at predetermined wavelengths; and
         a fiber optic for connecting the spectroscope to the measuring cell; and
      a physical property-predicting model;
   measuring light components for absorbance at predetermined wavelengths in an on-line manner in the liquified gas-collecting cylinder, said gaseous components being distilled at the first time from a crude oil sample upon distillation;
   measuring distillates of the distillate-collecting cylinders, in sequence, for absorbance at predetermined wavelengths;
   predicting physical properties of the distillate samples from the spectrum data on the basis of the chemometrics theory; and
   producing assay data for crude oils from the predicted physical properties.

2. The automatic analysis method as set forth in claim 1, wherein the spectroscopy utilizes a near infrared spectrometer, an infrared spectrometer, a Raman spectrometer, or an NMR spectrometer.

3. The automatic analysis method as set forth in claim 1, wherein the separation column part comprises at least two separation columns for distillates separated at not higher than 400° C. and at higher than 400° C., respectively, said two columns being alternatively operated under the control of a shutoff valve.

* * * * *